(12) United States Patent
Yanaki

(10) Patent No.: US 9,913,973 B2
(45) Date of Patent: Mar. 13, 2018

(54) TRANSCRANIAL DIRECT CURRENT BRAIN STIMULATION APPARATUS

(71) Applicant: Jamal S. Yanaki, Salt Lake City, UT (US)

(72) Inventor: Jamal S. Yanaki, Salt Lake City, UT (US)

(73) Assignee: Yani Skincare, LLC, West Valley City, UT (US)

( * ) Notice: Subject to any disclaimer, the term of this patent is extended or adjusted under 35 U.S.C. 154(b) by 333 days.

(21) Appl. No.: 13/868,909

(22) Filed: Apr. 23, 2013

(65) Prior Publication Data

US 2014/0316505 A1  Oct. 23, 2014

(51) Int. Cl.
*A61N 1/00* (2006.01)
*A61N 1/04* (2006.01)
*A61N 1/36* (2006.01)

(52) U.S. Cl.
CPC ......... *A61N 1/0456* (2013.01); *A61N 1/0496* (2013.01); *A61N 1/048* (2013.01); *A61N 1/36014* (2013.01); *A61N 1/36025* (2013.01)

(58) Field of Classification Search
CPC .... A61N 1/0456; A61N 1/0496; A61N 1/048; A61N 1/36014; A61N 1/36025; A61N 1/0526; A61N 1/0492
See application file for complete search history.

(56) References Cited

U.S. PATENT DOCUMENTS

| | | | |
|---|---|---|---|
| 4,570,637 A * | 2/1986 | Gomes | A61N 1/0492 600/395 |
| 6,233,489 B1 * | 5/2001 | Shealy | A61N 1/36014 128/898 |
| 2008/0319515 A1* | 12/2008 | Priori | A61N 1/20 607/75 |
| 2011/0144716 A1* | 6/2011 | Bikson | A61N 1/0529 607/45 |
| 2011/0306921 A1* | 12/2011 | Hawley | A61F 13/0273 604/20 |
| 2011/0319975 A1* | 12/2011 | Ho | A61N 1/0408 607/139 |
| 2012/0209346 A1* | 8/2012 | Bikson | A61N 1/08 607/45 |
| 2013/0035734 A1* | 2/2013 | Soler Fernandez | A61N 1/36025 607/3 |
| 2014/0148872 A1* | 5/2014 | Goldwasser | A61N 1/36082 607/45 |

* cited by examiner

*Primary Examiner* — Michael Carey
*Assistant Examiner* — Elizabeth K So
(74) *Attorney, Agent, or Firm* — Terrence J. Edwards; TechLaw Ventures, PLLC

(57) ABSTRACT

The present invention generally relates to the use of electrodes with human and animal subjects. More particularly, the present invention relates to electrical contacts which are applied to the surface of a subject for the purpose of delivering transranial direct current stimulation (TDCS).

5 Claims, 6 Drawing Sheets

TRANSCRANIAL DIRECT CURRENT BRAIN STIMULATION APPARATUS

FIELD

The present invention generally relates to the use of electrodes with human and animal subjects. More particularly, the present invention relates to electrical contacts which are applied to the surface of a subject for the purpose of delivering transcranial direct current stimulation (TDCS).

BACKGROUND

Application of electrical currents to modify brain function has been practiced for a very long time. Systematic animal studies in anesthetized rats demonstrated that weak direct currents, delivered by intracerebral or epidural electrodes, induce cortical activity and excitability diminutions or enhancements, which can be stable long after the end of stimulation. The long-lasting effects can be used to alter neural activity and behavior. Initial studies in humans aimed at treating or modifying psychiatric diseases, particularly depression, suggested diminished depressive symptoms, and reduced manic symptoms. In the last few decades, TDCS was re-evaluated and shown to reliably modulate human cerebral cortical function inducing focal, prolonged but yet reversible shifts of cortical excitability.

Studies combining TDCS with other brain imaging and neurophysiologic mapping methods (such as MRI, PET, EEG) promise to provide invaluable insights on the correlation between modification of behavior and its underlying neurophysiologic underpinnings. Depending on where the anode and cathode electrodes are placed on the head of a patient, studies show that various disorders and behaviors can be treated using TDCS by stimulating different parts of the brain. In some instances, the polarity of the electrodes, along with the placement, can affect the type of condition and area of the brain to be treated.

Current electrodes used with TDCS often use a carbon or steel mesh electrode with a sponge and saline or other medium to achieve an electrical connection between the electrodes through skin (and/or hair). However, the electrodes used tend to cause skin irritation because the current tends to achieve some degree of hydrolysis in the saline resulting in a pH change in the saline solution (or other conductive medium), which tends to irritate the skin causing discomfort to the patient.

BRIEF SUMMARY

Methods, systems, and electrode patches for transcranial direct current stimulation (TDCS) are disclosed. Systems for transdermal direct current stimulation system for applying a current to pass through the tissues of a patient may include, an electric current generator, and at least two electrode patches configured to be electrically connected to the current generator and affixed to a patient such that current passes through the tissues of the patient when the at least two electrode patches are affixed to the patient. At least one of the at least two electrode patches may include a flexible, planar biocompatible substrate, a planar solution matrix having on respective opposite sides thereof a skin contact surface and a securement surface, a portion of the securement surface being retained against the substrate, the skin contact surface of the solution matrix being configured to effect an electrically conductive engagement with skin of a patient, and an electrode configured to transmist current from the current generator to the solution matrix.

The electrode may include, a planar electrically conductive backing layer having a driving face, a planar pH-control layer formed on the driving face of the backing layer, the pH-control layer comprising Ag and AgCl, the backing layer and the pH-control layer being located between the substrate and the solution matrix, the pH-control layer being entirely covered by the solution matrix, and an electrical contact extending from the pH-control layer through an opening in the substrate, the electrical contact being configured to be selectively coupled to the current generator.

In some embodiments, systems may also include a saline solution (including water) within the solution matrix. At least a portion of the electrical contact may comprise Ag and Ag/Cl. The pH-control layer may be formed by printing or depositing the Ag and AgCl directly onto the backing layer. The backing layer may comprise carbon or copper. The backing layer may also be printed or deposited directly onto the substrate. The pH-control layer may also form a repeating pattern having apertures in the pH-control layer.

Some embodiments of methods of treating a patient using transdermal direct current stimulation may include, providing a current generator, connecting an anode to the patient, connecting a cathode to the patient such, wherein at least one of the anode and cathode is a pH-controlling electrode comprising a pH-control layer comprising Ag and AgCl and a solution matrix comprising water, and connecting the current generator to each of the anode and cathode. Exemplary methods may further include, applying between about 0.5 and 3 mA of current through the patient. The current may be applied for between 10 and 40 minutes, and may be applied between 1 and 20 times each week for at least two weeks.

In some embodiments, the connecting the anode or connecting the cathode comprising snapping a wire having a snap connector onto the electrical contact. The anode and the cathode may be connected to the head of the patient. Attaching the anode and the attaching the cathode may be performed using a device extending around at least a portion of the head of the patient. The location of the anode and cathode on the patient may be based on a desired portion of the brain to be treated.

Additional features and advantages are provided in the description which follows, and in part will be obvious from the description, or may be learned by the practice of the described embodiments. The features and advantages may be realized and obtained by means of the instruments and combinations particularly pointed out in the appended claims. These and other features will become more fully apparent from the following description and appended claims, or may be learned by the practice of the embodiments as described.

BRIEF DESCRIPTION OF THE DRAWINGS

In order to describe the manner in which the above-recited and other advantages and features of the invention can be obtained, a more particular description of the invention briefly described above will be provided by reference to specific embodiments which are illustrated in the appended drawings. The drawings depict only typical and exemplary embodiments and are not, therefore, to be considered to be limiting of its scope. Aspects of the disclosed embodiments will be described and explained with additional specificity and detail through the use of the accompanying drawings in which:

FIGS. 2-4a, and 5a illustrate various projections exemplary electrode patches;

FIG. 4b illustrates an exploded view of the exemplary electrode patches of FIGS. 2-4a;

FIG. 5b illustrates an exploded view of the exemplary electrode patch of FIG. 5a;

DETAILED DESCRIPTION

The following description supplies specific details of TDCS systems and electrodes for use in TDCS, including methods of making and using the systems and electrodes, in order to provide a thorough understanding. Nevertheless, the skilled artisan would understand that the electrodes and associated methods of using them can be implemented and used without employing these specific details. Indeed, the electrodes and associated methods can be placed into practice by modifying the embodiments shown in the figures and associated methods of using those embodiments, and can be used in conjunction with any apparatus and techniques conventionally used in the industry.

Figure 1:
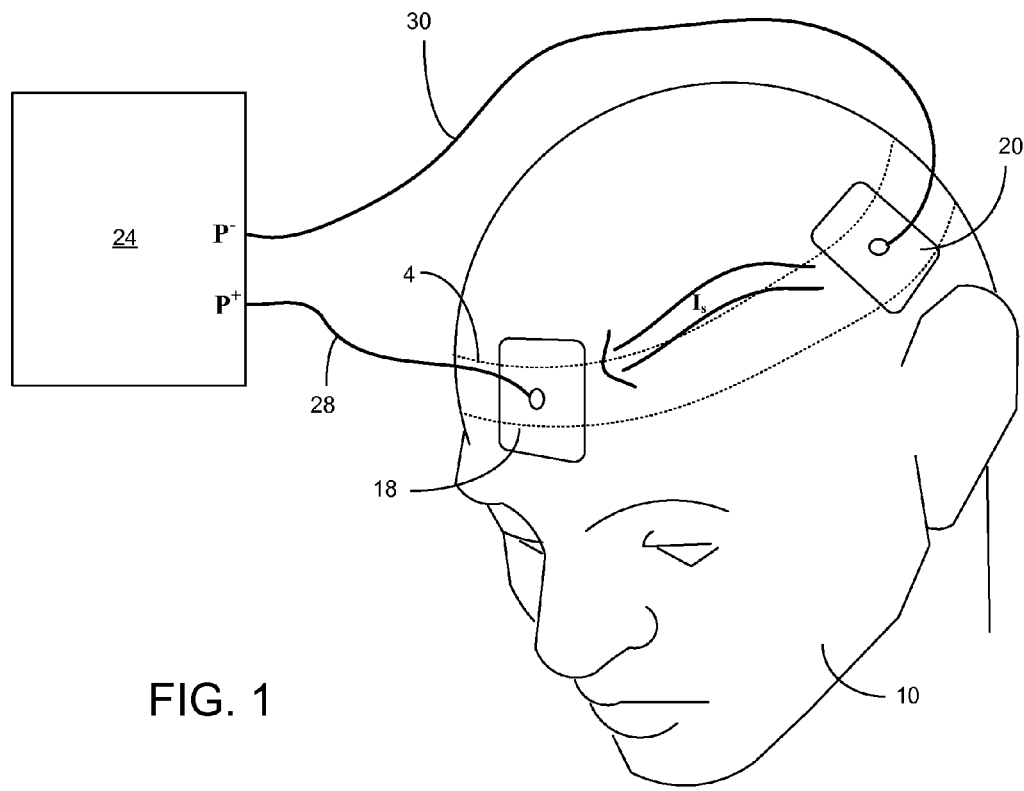
FIG. 1 illustrates an exemplary TDCS system.

FIG. 1 shows a patient 10 receiving TDCS therapy. For that purpose, patient 10 may be wearing components of an embodiment of an TDCS system 17 with exemplary electrode patches 18, 20. The active electrode patches 18, 20 may be held in place on patient 10 with headband 4. These components of delivery system 17 include a active electrode patches 18, 20 attached to the head of patient 10. Electrode patches 18, 20 may be removably adhered to the skin of patient 10 at these respective locations, or other locations as desired to treat a particular condition, and a current may be made to flow between electrode patches 18, 20 through the skin, tissue, and brain of patient 10 along current path $I_S$ by appropriately coupling to each of electrode patch 18, 20 an external power source 24 shown schematically in FIG. 1.

Power source 24 may be powered from a wall outlet, or may be battery powered. Power source 24 may include a positive pole $P^+$, an associated positive lead 28, a negative pole $P^-$, and an associated negative lead 30. In FIG. 1, positive lead 28 and negative lead 30 of power source 24 are connected to electrode patches 18, 20, respectively.

In some embodiments, electrode patches 18, 20 may be structurally the same, or may be different according to various embodiments described below. Similarly, one of the electrode patches may be a simple auxiliary patch if there is no need to provide a solution with the electrode based on the placement of the electrode. For the purposes of this disclosure, electrode patch 18 will be discussed in detail.

Electrode patch 18 may be attached to positive pole $P^+$ of power source 24 by way of positive lead 28. Similarly, negative lead 30 may be used to electrically couple negative pole $P^-$ of power source 24 to electrode patch 20. Electrode patch 20 carries a return electrode by which the electrical potential at the other pole of power source 24 may be communicated to the skin of patient 10 at a contact location remote from electrode patch 18 to provide a pathway for current flow $I_S$. The placement of electrode patches 18, 20 may be provided based on the areas of the brain that are desired to be stimulated by current flow $I_S$.

In electrical circuits, the flow of current is conventionally indicated as a flow of electrons through the circuit from the positive to the negative pole of the power source employed therewith. Therefore, current $I_S$ is schematically indicated by an arrow to flow through patient 10 from electrode patch 18, which may be associated with positive pole $P^+$ of power source 24 in FIG. 1, to electrode patch 20, which may be associated with negative pole $P^-$ of power source 24.

The negative pole $P^-$ of power source 24 of FIG. 1 may be coupled by way of negative lead 30 to stud 60 (shown in FIGS. 2-5b) of electrode patch 20 to patient 10 at a first contact location. The positive pole $P^+$ of power source 24 may be correspondingly coupled to electrode patch 18 and therefrom through solution matrix 46 (shown in FIGS. 2-5b) to skin at a second contact location remote from electrode patch 18. Aside from the conductivity of the patient 10, the first contact location and the second contact location are electrically isolated from each other.

Power source 24 may be a current generator that provides a therapeutically sufficient current to treat patient 10. For example, in some embodiments, power source 24 may provide between 0.1 mA and 100 mA current flow. In an example of a treatment regimen, a patient may undergo a treatment of 1-2 mA for 20 minutes 5-10 times each week, as desired. Of course, the amount of current, placement of electrodes, duration and frequency of treatment, will all be determined based on the understood best practices by those of ordinary skill for treatment using TDCS.

Figure 2:
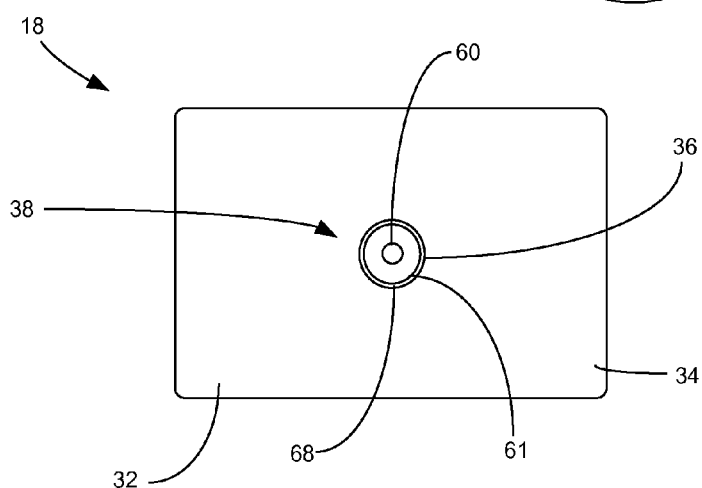
Figure 3:
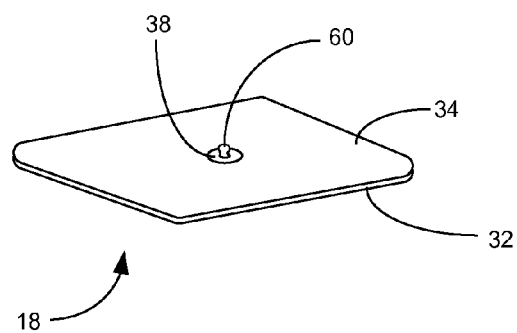

FIGS. 2-5 taken together afford an overview of the structure of embodiments of electrode patch 18, and, if desired electrode patch 20. FIG. 2 is a top view of electrode patch 18 showing the surface of electrode patch 18 that may be exposed when electrode patch 18 may be worn by patient 10 in the manner illustrated in FIG. 1. Similarly, FIG. 3 is a perspective view of electrode patch 18. Electrode patch 18 may include a flexible, planar biocompatible, non-electrically conductive, substrate 32 that has an upper face 34 that may be visible when worn by patient 10. Formed though substrate 32 at a location convenient to the overall construction and functioning of electrode patch 18 may be an electrical access aperture 36 through which projects an electrical contact 38 of the type to which electrical leads, such as positive lead 28 and negative lead 30 of power source 24, can be readily secured and non-destructively disengaged as needed, such as stud 60 as illustrated.

Figure 4A:
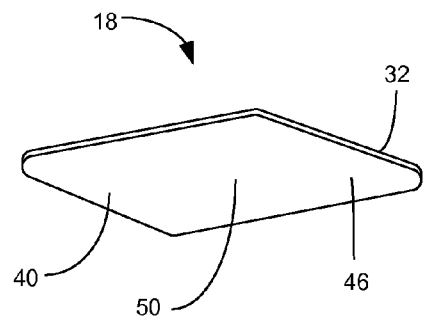

FIG. 4a is a perspective view of electrode patch 18 taken from the side of electrode patch 18 opposite from upper face 34 shown in FIG. 2. Revealed thusly may be a therapeutic face 40 of substrate 32 that may be intended to be disposed in contact with the skin or hair of a patient, such as patient 10 in FIG. 1. Solution matrix 46 may be visible on therapeutic face 40. Solution matrix 46 can take the form of a gel suspension or of an absorbent pad of gauze or cotton that may be saturated at some time prior to use with a fluid solution to facilitate electrical conductivity between electrical contact 38 and the skin, or the skin through the hair as a fluid solution may provide an electrical pathway from electrical contact 38 and the skin. When permeated by a solution, solution matrix 46 functions as a conductive pathway and reservoir of solution during treatment. In some embodiments, the fluid solution may be simple water or a saline solution, or any other solution that creates the desired pathway.

Figure 4B:
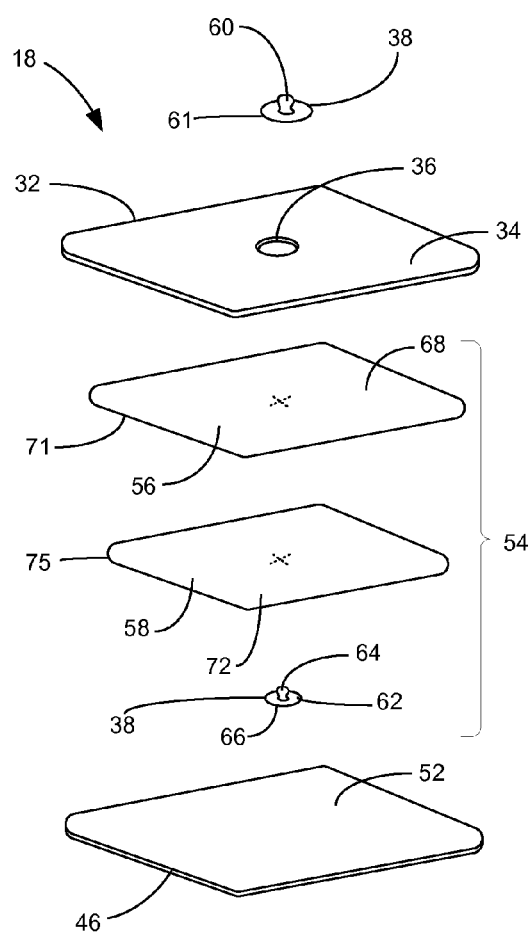
Figures 5A, 5B:
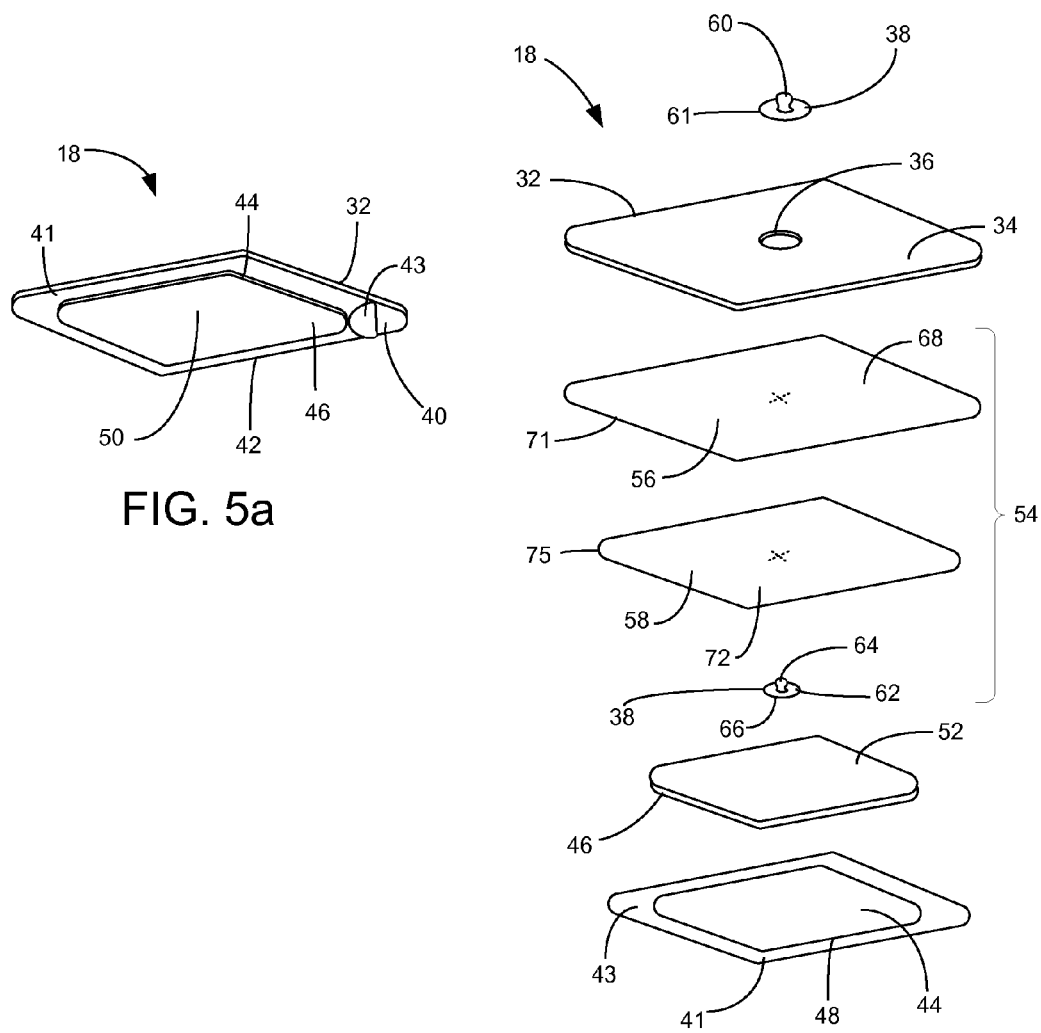

In some embodiments, electrode patches 18, 20 may be held in place with a adhesive tape, a harness, mask, cap, or other external mechanism, such as the embodiment shown in FIGS. 4a-4b, or it may be held in place using adhesive integral to the electrode patch, such as is shown in FIGS. 5a-5b. In such embodiments, therapeutic face 40 may be at least partially coated with a biocompatible adhesive to a sufficient extent as will enable therapeutic face 40 to be removably secured to the person of patient 10.

As is shown in FIG. 5a, the adhesive on therapeutic face 40 may be shielded by a removable release liner 41, which may be peeled from therapeutic face 40. Release liner 41 may have on the opposite sides thereof, respectively, first an exposed face 42 and second a contact face 43 that actually engages the adhesive on therapeutic face 40 of substrate 32. Release liner 41 may include opening 44 for solution matrix 46 in such embodiments. As shown in FIG. 5a, opening 44 may be substantially filled by a generally planar solution matrix 46 that exhibits a generally rectangular periphery 48. Solution matrix 46 may project through opening 44 in such a manner that the surface, while oriented generally parallel to the plane of release liner 41 and the plane of therapeutic face 40 of substrate 32, extends away from the adhesive surface a distance that is approximately equal to the thickness of solution matrix 46.

The side of solution matrix 46 visible in FIGS. 4a and 5a may form a corresponding skin contact surface 50. By way of skin contact surface 50, solution matrix 46 may be intended to electrically conductively engage the skin of a patient, when therapeutic face 40 of substrate 32 may be disposed against and removably adhered to the person of the patient.

As shown in FIG. 5a-5b, opening 44 in release liner 41 and solution matrix 46 on therapeutic face 40 of substrate 32 may be closely similar in size and shape. As a result, the edges of opening 44 may be in close proximity to periphery 48 of solution matrix 46, when contact face 43 of release liner 41 may be disposed covering the adhesive on the portion of therapeutic face 40 located between periphery 48 of solution matrix 46 and periphery of therapeutic face 40. Consequently, release liner 41 may cover the entirety of that defined above as being the exposed adhesive portion of therapeutic face 40.

Opening 44 in release liner 41 may afford unimpeded access by medical personnel to the entirety of skin contact surface 50 of solution matrix 46 prior to the removal of release liner 41 from therapeutic face 40. Additionally, the near congruency of periphery 48 of skin contact surface 50 of solution matrix 46 with opening 44 in release liner 41 advantageously allows release liner 41 to protect the adhesive on the exposed portion of therapeutic face 40 from any solution that might overflow from solution matrix 46 during the process of wetting solution matrix 46 in anticipation of use.

FIGS. 4b and 5b are exploded views of electrode patch 18 taken from the perspective of electrode patch 18 shown in FIGS. 4a and 5a, respectively. Shown accordingly in are upper face 34 of substrate 32, and in FIG. 5b, contact face 43 of release liner 41. Newly revealed on the side of solution matrix 46 opposite from skin contact surface 50, which does not appear in FIGS. 4b, 5b, may be a securement surface 52 of solution matrix 46 by which solution matrix 46 may be retained on therapeutic face 40 of substrate 32.

Also revealed in the exploded views are the components of an active electrode 54. While not visible in the assembled condition of electrode patch 18 illustrated in FIGS. 2, 3, 4a and 5a, in the assembled condition of electrode patch 18 active electrode 54 may be sandwiched between solution matrix 46 and the portion of therapeutic face 40 of substrate 32 concealed by solution matrix 46. Active electrode 54 may include a backing layer 56, a pH-control layer 58, and electrical contact 38, which may be itself a two-piece assembly. One component of electrical contact 38 may be a hollow stud 60 having a periphery 61 and an open end that is not visible in FIGS. 4a and 5a. In addition, electrical contact 38 may include a cooperating eyelet 62 that may have a shaft 64 configured for press fit insertion through the open end of stud 60 and a generally planar flange 66 secured to an end of shaft 64.

The side of backing layer 56 shown in FIG. 5 functions as a securement surface 68 of backing layer 56 by which backing layer 56 engages and may be attached to therapeutic face 40 of substrate 32. In so doing, backing layer 56 may be positioned across electrical access aperture 36. Thus, in FIG. 2, a small portion of securement surface 68 of backing layer 56 may be visible from upper face 34 of substrate 32 through electrical access aperture 36 between substrate 32 and periphery 61 of stud 60. The opposite side of backing layer 56, which is not shown in FIGS. 4b, 5b, defines a driving face of backing layer 56 that at least in part contacts securement surface 52 of solution matrix 46 in the assembled condition of electrode patch 18 shown in FIGS. 2-4a, 5a. Backing layer 56 has a periphery 71 that appears to be generally rectangular as illustrated, but that may assume many other configurations, such as circular, hexagonal, square, trapezoidal, oblong, ovoid, or any other suitable shape.

Correspondingly, the side of pH-control layer 58 presented to view in FIG. 5 may be a securement surface 72 of pH-control layer 58. All or some of securement surface 72 abuts a portion only of the driving face of backing layer 56 in the assembled condition of active electrode 54. Any portion of securement surface 72 of pH-control layer 58 that does not abut the driving face of backing layer 56 may eventually become attached to therapeutic face 40 of substrate 32 in the assembled condition of electrode patch 18. The opposite side of pH-control layer 58, which is also not visible in FIG. 5, defines a driving face of pH-control layer 58. Driving face of pH control layer 58 may engage securement surface 52 of solution matrix 46 in the assembled condition of electrode patch 18. Finally, pH-control layer 58 may have a periphery 75 that may be similar to periphery 71 of backing layer 56. Nonetheless, periphery 75 of pH-control layer 58 may assume many other configurations and need not echo the configuration of periphery 71 of backing layer 56 in any manner whatsoever.

One method for making a electrode patch, such as electrode patch 18, will be described. In that method, the manufacture of active electrode 54 precedes the assembly of active electrode 54 with the other elements of electrode patch 18 shown in FIG. 5.

In active electrode 54, pH-control layer 56 may be made of an electrically conductive material that is, under conditions of current flow through electrode patch 18, capable of moderating changes in the hydrogen-ion concentration, or the pH, in solution matrix 46. Moderating changes in the hydrogen-ion concentration in solution matrix 46 may be equivalent to moderating the hydroxyl-radical concentration in solution matrix 46. Current arises when electrode patch 18 may be adhered to the skin of a patient, and an electrical potential may be imposed between active electrode 54 and the skin of the patient at a contact location remote from solution matrix 46.

The ability of pH-control layer 58 to moderate changes in the hydrogen-ion concentration in solution matrix 46 can be achieved in a number of different ways through the use of various materials to construct pH-control layer 58. For example, the material of which pH-control layer 58 may be formed can be a material that may be capable of precluding the electrolysis of the water ($H_2O$) in solution matrix 46 by competing to be electrolyzed instead of that water during iontophoretic current flow. Examples of such materials include a mixture of silver (Ag) and silver-chloride (AgCl) or a mixture of potassium (K) and potassium-chloride (KCl). These materials electrolyze before water and when so doing produce constituent chemical components that do not change the pH in solution matrix 46. Alternatively, the material of which pH-control layer 58 may be formed may be capable of neutralizing the chemical products created by the electrolysis of water in solution matrix 46 during current flow. An example of such a material is potassium phosphate ($K_3PO_4$).

Backing layer 56 may be made from a film of a more common electrically conductive material, such as carbon (C), copper (Cu), aluminum (Al), or rubberized carbon. Backing layer 56 may have a thickness in a range from about 1.0 millimeter to about 5.0 millimeters. The material of pH-control layer 58 may be applied to the driving face of backing layer 56, by printing or by deposition through a mask shaped to correspond to that intended in pH-control layer 58. In other embodiments, backing layer may be provided as a sheet and then cut to the desired shape. In some embodiments, pH-control layer 58 covers less than all of the driving face of backing layer 56. As a result, all of pH-control layer 58, but only the portion of the driving face of backing layer 56 that may be free of pH-control layer 58, may be able to electrically engage securement surface 68 of solution matrix 46, when active electrode 54 is assembled with the other elements of electrode patch 18. Similar to backing layer 56, pH control layer 58 may be printed, deposited directly onto, or otherwise formed on backing layer 56. In some embodiments, a film of pH control layer may be cut and adhered to backing layer 56.

To complete the manufacture of active electrode 54, the components of electrical contact 38 may fitted together with pH-control layer 58 and backing layer 56 sandwiched therebetween. The free end of shaft 64 of eyelet 62 may be forced through pH-control layer 58 at a generally central location and then through backing layer 56 at a generally central location. Alternatively, apertures through which to advance shaft 64 may be formed in advance through an appropriate location in one or both of pH-control layer 58 and backing layer 56. Finally, the free end of shaft 64 of eyelet 62 may be inserted into the open end of stud 60. By press fitting or by other appropriate arrangements, eyelet 62 becomes permanently secured thereto. Backing layer 56 and pH-control layer 58 are thereby clamped between stud 60 and flange 66 of eyelet 62, and the assembly of active electrode 54 is complete.

Stud 60 may be made of an electrically conductive material. Therefore, once the assembly of active electrode 54 is complete, stud 60 may be correspondingly electrically coupled to backing layer 56. As mentioned earlier, backing layer 56 and pH-control layer 58 are both made of electrically conductive materials. Accordingly, in the assembled condition of active electrode 54, stud 60 becomes electrically coupled to the entirety of backing layer 56, including in particular driving face of backing layer 56. Stud 60 may be also electrically coupled to the entirety of pH-control layer 58. Active electrode 54 may be thus a single, electrically conductive structure that communicates through solution matrix 46 the electrical potential that may be applied to stud 60 from power source 24 shown in FIG. 1. The electrical potential may be, either a positive electrical polarity that may be provided through positive lead 28, or a negative electrical polarity that may be provided through negative lead 30. The types of material that may be used as eyelet 62 warrant discussion.

Eyelet 62 can be made of an electrically conductive material, possibly even the same type of electrically conductive material as that from which stud 60 may be manufactured. Then, with shaft 64 of eyelet 62 engaged in stud 60 in the assembled condition of electrical contact 38, any electrical potential applied to stud 60 from power source 24 may be directly communicated to the entirety of electrical contact 38, including in particular to flange 66 of eyelet 62. In the assembled condition of electrode patch 18, flange 66 of eyelet 62 may directly engage securement surface 52 of solution matrix 46.

In the assembled condition of electrode patch 18, the presence of flange 66 on driving face 74 of pH-control layer 58 may impede the migration of the chemical constituents of pH-control layer 58 into the region of solution matrix 46 that may be located on the opposite side of flange 66 from pH-control layer 58. These are the material that are intended to moderate changes in the hydrogen-ion concentration, or the pH, in solution matrix 46 during iontophoretic current flow. Regions of solution matrix 46 are thus eclipsed by flange 66 from the full beneficial pH moderating effects that are intended to be exercised upon solution matrix 46 by pH-control layer 58. As a result, these eclipsed regions of solution matrix 46 are more likely to become caustic during the course of iontophoretic current flow than may be the balance of solution matrix 46. The regions of solution matrix 46 thusly eclipsed by flange 66 may be inclined to exhibit pH instability, and the portion of skin contact surface 50 of solution matrix 46 adjacent to those regions may be correspondingly inclined to irritate the skin against which electrode patch 18 is disposed.

This problem of localized regions of pH instability in skin contact surface 50 of solution matrix 46 may be exacerbated when eyelet 62 of electrical contact 38 may be constructed from an electrically conductive material.

Then, the electrical potential applied to stud 60 from power source 24 may be directly communicated to flange 66, which may be in turn in an abutting relationship to securement surface 52 of solution matrix 46. The electric field associated with flange 66 may be imposed on the region of solution matrix 46 opposite thereto with an intensity that may be greater than the intensity imposed on solution matrix 46 by active electrode 54 as a whole. This unevenness in the intensity of the electric field throughout solution matrix 46 causes a corresponding disparity in the rate of electrolysis of the water at locations in solution matrix 46. In particular, the rate of electrolysis of water may be accelerated in the region of solution matrix 46 that may be directly opposite from flange 66 of electrical contact 38. This is, however, the very region of solution matrix 46 in which pH instability is most likely, due to the eclipsing of a portion of the driving face of pH-control layer 58 by flange 66 in the manner discussed above. To ameliorate these conditions, flange 66, or at least the surface thereof that engages securement surface 52 of solution matrix 46, may be coated with a material of the types disclosed above (such as Ag/AgCl) by which pH-control layer 58 may be rendered capable of moderating changes in the hydrogen-ion concentration in solution matrix 46.

According to another embodiment of an active electrode, active electrode 54, eyelet 62, or at least flange 66 thereof, may be comprised of an electrically insulative material. Then coating flange 66 with a material that moderates changes in the hydrogen-ion concentration in solution matrix 46 may not be warranted. When eyelet 62, or at least flange 66 thereof, is comprised of an electrically insulative material, the electrical potential applied to stud 60 may not be communicated to flange 66, and no unusual acceleration of the electrolysis of water should then result in regions of solution matrix 46 that are directly opposite from flange 66.

An assembled active electrode 54 may be combined in the following manner with the other elements of electrode patch 18 shown in FIGS. 4b, 5a. Sheeting of a flexible biocompatible material may be cut into the shape of substrate 32, electrical access aperture 36 may be formed therethrough, and an adhesive may be applied to the side that is intended to function as therapeutic face 40. These steps can be performed in any order that is most convenient and economical. Active electrode 54 may be then disposed against the adhesive on therapeutic face 40 of substrate 32 in such a manner that stud 60 of electrical contact 38 projects through electrical access aperture 36 in substrate 32 in the manner shown in FIG. 2.

An absorbent material, such as gauze or cotton, may be cut or otherwise configured into the shape desired in solution matrix 46. Solution matrix 46 can alternatively be formed from a medical grade gel, such as a hydro gel, or any substance that will adequately form a conductive relationship. In any case, solution matrix 46 may be then attached by securement surface 52 thereof to therapeutic face 40 of substrate 32, by the adhesive on therapeutic face 40, or through any other arrangement. In the process, that solution matrix 46 should generally completely cover active electrode 54.

The portion of therapeutic face 40 thereby obscured by solution matrix 46 defines a concealed portion of therapeutic face 40, while the portion of therapeutic face 40 other than the concealed portion thereof defines an exposed portion of therapeutic face 40. It should be noted that all of therapeutic face 40, or the portion of therapeutic face 40 contacted by active electrode 54 may also be covered, and therefore obscured, by solution matrix 46. Therefore, the portions of therapeutic face 40 contacted by active electrode 54 directly, as well as that contacted by solution matrix 46 directly may be included in the concealed portion of therapeutic face 40 as defined above.

Finally, thin nonabsorbent sheeting of a flexible biocompatible material may be cut into the shape of release liner 41, opening 44 may be formed therethrough, and contact face 43 of release liner 41 may be disposed on the adhesive on the exposed portion of therapeutic face 40 with solution matrix 46 projecting in close conformity through opening 44. To the extent practicable, no portion of solution matrix 46 should generally be obscured by release liner 41 in embodiments where release liner 41 is used. As a result, the full extent of skin contact surface 50 of solution matrix 46 will remain accessible to medical personnel, even while release liner 41 remains in covering engagement with therapeutic face 40. The portions of contact face 43 of release liner 41 immediately adjacent to opening 44 are then, temporarily adhered to the adhesive on therapeutic face 40 immediately adjacent to periphery 48 of solution matrix 46. In this manner, a fluid tight seal may be effected on behalf to the entirety of the exposed portion of therapeutic face 40 between from any fluid in or intended for solution matrix 46.

Figure 6:
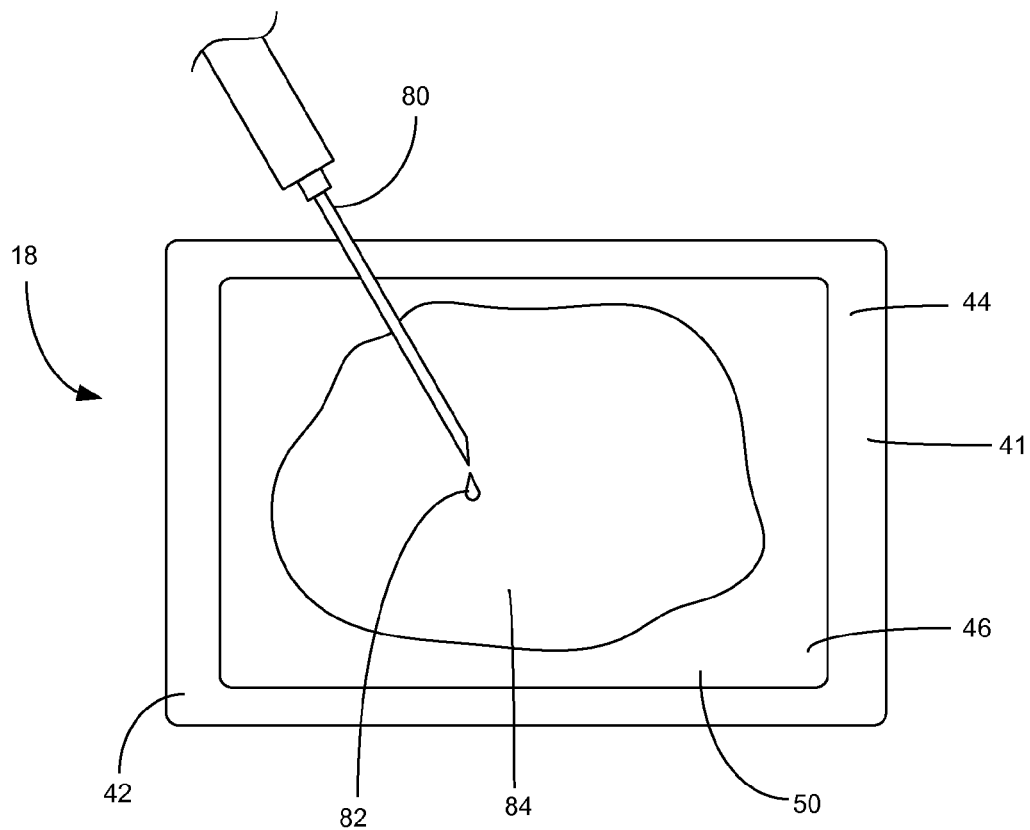
FIG. 6 illustrates an exemplary embodiments of an electrode patch receiving a solution.

FIG. 6 is a plan view of the side of electrode patch 18 from which solution matrix 46 may be visible projecting through opening 44 in release liner 41. Also shown is a syringe 80 containing a solution 82 that is being used to saturate solution matrix 46 in anticipation of the use of electrode patch 18. Drops of solution 82 may be deposited on skin contact surface 50 of solution matrix 46 and permitted to soak thereinto.

As this process progresses, a saturated portion 84 may develop in solution matrix 46 and grow laterally as additional drops of solution 82 are added to solution matrix 46. Saturated portion 84 of solution matrix 46 may be visually distinguishable by a medical practitioner from the unsaturated portions of solution matrix 46. As solution matrix 46 may be generally uncovered by release liner 41, a medical practitioner may thereby be able to observe the enlargement of saturated portion 84 of solution matrix 46 as drops of solution 82 are added thereto, eventually verifying by visual inspection when the entirety of solution matrix 46 becomes adequately wetted.

It is not uncommon that solution matrix 46 may become locally oversaturated in some areas during this wetting process. Then, solution 82 may overflow solution matrix 46. This overflow of solution 82 may be prevented from coming into contact with the adhesive on substrate 32 because the overflow may be deposited on exposed face 42 of release liner 41.

In the alternative to using a syringe of solution, the wetting of solution matrix 46 can be accomplished through the bursting onto the medicament matrix of a capsule or blister of solution that constitutes an integral component of the electrode patch, an element of the packaging for the electrode patch, or a article distinct from both.

As shown in the Figures, active electrode 54 may be sandwiched between solution matrix 46 and therapeutic face 40 of substrate 32 interior of periphery 48 of solution matrix 46. Stud 60 of electrical contact 38 of active electrode 54 may project through electrical access aperture 36 in substrate 32 and away from skin, thereby being easily accessible for electrical connection to a lead from a source of electrical power. To maintain this desired position of active electrode 54 relative to the other elements of electrode patch 18, securement surface 68 of backing layer 56 of active electrode 54 may be adhered to therapeutic face 40 of substrate 32 in the vicinity of electrical access aperture 36. Solution matrix 46 may be then adhered to at least a portion of therapeutic face 40 of substrate 32 surrounding active electrode 54. Active electrode 54 may be thereby precluded from effecting direct electrical contact with skin against which electrode patch 18 is disposed.

Among the elements of active electrode 54, pH-control layer 58 may cover less than all of the driving face of backing layer 56, the portions not overlaid by pH-control layer 58 remain capable of effecting direct electrical contact with solution matrix 46. The role of backing layer 56 in active electrode 54 may be that of communicating to solution matrix 46 the electrical potential that may be applied to stud 60 of electrical contact 38. As backing layer 56 may be constructed from an electrically conductive material, that electrical potential may be communicated to solution matrix 46 directly through the portions of backing layer 56 uncovered by pH-control layer 58 and through the driving face of backing layer 56. As pH-control layer 58 may be also made of an electrically conductive material, the portion of the driving face of backing layer 56 that may be covered by pH-control layer 58 participates in this function indirectly through pH-control layer 58.

The role of pH-control layer 58 in active electrode 54 may be that of moderating changes in the hydrogen-ion concentration, or the pH, developed in solution matrix 46 during the flow of skin current $I_S$. The entry of a second constituent current into pH-control layer 58 from solution matrix 46 causes some of the material of which pH-control layer 58 may be comprised to migrate out of pH-control layer 58 and into solution matrix 46 as an ionic flow. Depending on the material composition chosen for pH-control layer 58 as described earlier, this ionic flow may serve in various ways to moderate changes in the hydrogen-ion concentration in solution matrix 46. For example, the materials in the ionic flow could preclude the electrolysis of the water in solution matrix 46 by competing to be electrolyzed instead of that water during iontophoretic current flow. Alternatively, the material in the ionic flow could neutralize the electrolysis products of water caused by iontophoretic current flow.

In this process, the material of which pH-control layer 58 may be comprised may gradually become depleted. Should pH-control layer 58 thereby become completely consumed, pH-control layer 58 will no longer be reliably conductive, and may even completely block the passage of current therethrough into backing layer 56. Skin current $I_S$ correspondingly may become irregular or cease entirely. In other terms, the electrical resistance of active electrode 54 may increase, possibly to an extent that current flow will terminate.

Against this possibility, pH-control layer 58 and backing layer 56 may be so sized and positioned relative to each other that pH-control layer 58 covers less than all of the driving face of backing layer 56. Then, regardless of the conditions of electrical conductivity in pH-control layer 58, the portion of the driving face of backing layer 56 not obscured by pH-control layer 58 may offer a conductive pathway for at least a portion of the current, and the continuity of at least some current flow may be insured. The electrically conductive pathway taken by first constituent current may be a relative low resistance pathway as compared to the conductive pathway taken through pH-control layer 58 even when the material of pH-control layer 58 has not been depleted by iontophoretic current flow to any significant degree.

Therefore, the design of active electrode 54 in such a manner that a portion of the driving face of backing layer 56 is covered by pH-control layer 58 may reduce the overall electrical resistance to current flow presented by active electrode 54. Indeed, the overall resistance of active electrode 54 can be adjusted appropriately in anticipation of specific therapy conditions by varying a pair of active electrode design criteria. The first criterion may be the ratio of the area of pH-control layer 58 to the total area of backing layer 56. The second criterion may be the ratio of the area of the exposed portion of backing layer 56 that is not covered by pH-control layer 58 to the area of pH-control layer 58. Examples of these ratios will be disclosed subsequently for a number of embodiments of active electrodes.

Before doing so, however, it should be recalled that the rate of electrolysis of water is accelerated in a region 104 of solution matrix 46 that is directly opposite from flange 66 of electrical contact 38, and that in region 104 there may be an increased likelihood of pH-instability due to the eclipsing of the driving face of pH-control layer 58 by flange 66 if flange 66 is electrically conductive or uncoated with a material of the types from which pH-control layer 58 is comprised. In some embodiments, where an amelioration of the effects of electrolysis and pH variation is a primary goal, it may be advantageous to cover the entire driving face of backing layer 56 to reduce the possibility of irritation to the skin of a user when pH-control layer 58 is consumed. As such, the amount and thickness of the pH-control layer 58 may be selected based on the expected time for a session of therapy.

FIGS. 7a-7f are plan views of individual embodiments of active electrodes taken from the side of each respective active electrode that engages solution matrix 46 in an active electrode patch. In each case, the active electrode depicted may be resting against or secured to the underlying therapeutic face 40 of a substrate of a electrode patch.

Figure 7A:
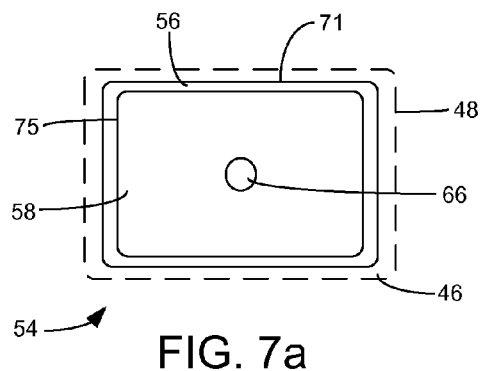
FIGS. 7a-7f illustrate various embodiments of layer design and positioning of exemplary electrode patches.

FIG. 7a is such a plan view of active electrode 54. Superimposed by way of reference in phantom on therapeutic face 40 is periphery 48 of solution matrix 46, which in the assembled condition of the electrode patch depicted would entirely obscure active electrode 54. This is borne out in FIG. 7a, as flange 66 of eyelet 62 of electrical contact 38, pH-control layer 58, and backing layer 56 of active electrode 54 are shown superimposed on one another in that order, with all of each of these components of active electrode 54 located interior of periphery 48 of solution matrix 46.

Periphery 71 of backing layer 56, periphery 75 of pH-control layer 58, and periphery 48 of solution matrix 46 may be generally rectangular in configuration. Nonetheless, periphery 71, periphery 75, and periphery 48 are not, and need not be, disposed in any concentric relationship to each other, or to flange 66 of eyelet 62 of electrical contact 38. The total area of backing layer 56 may be greater than the area of pH-control layer 58. Periphery 75 of pH-control layer 58 may be disposed entirely within periphery 71 of backing layer 56, and backing layer 56 may have an exposed annular area between periphery 75 of pH-control layer 58 and periphery 71 that is not covered by pH-control layer 58.

Figure 7B:
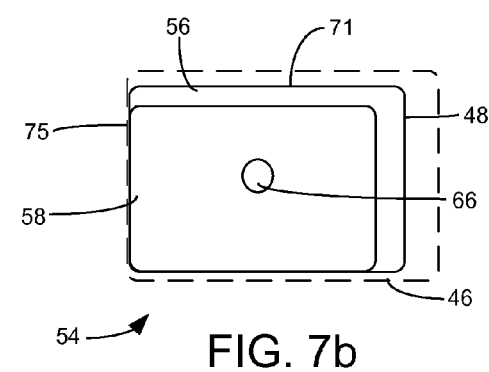

FIG. 7b is a plan view of an embodiment of an active electrode 54. Superimposed by way of reference in phantom may be periphery 48 of solution matrix 46, which in the assembled condition of the electrode patch depicted would entirely obscure active electrode 54. Active electrode 54 may be made up of the same elements, namely flange 66 of eyelet 62, pH-control layer 58, and backing layer 56, as were employed in the embodiment shown in FIG. 7a. In contrast thereto, however, these elements are more pronouncedly eccentrically positioned relative to each other and to periphery 48 of solution matrix 46 than was the case relative to active electrode 54 in FIG. 7a.

In FIG. 7b, periphery 75 of pH-control layer 58 may tangentially engage periphery 71 of backing layer 56, and periphery 71 of backing layer 56 may tangentially engage periphery 48 of solution matrix 46. As thusly arranged, solution matrix 46 may nonetheless entirely obscure active electrode 54. The total area of backing layer 56 may then remain greater than the area of pH-control layer 58, and backing layer 56 may have an exposed area not covered by pH-control layer 58 between periphery 75 of pH-control layer 58 and periphery 71 of backing layer 56, although such need not be the case.

Figure 7C:
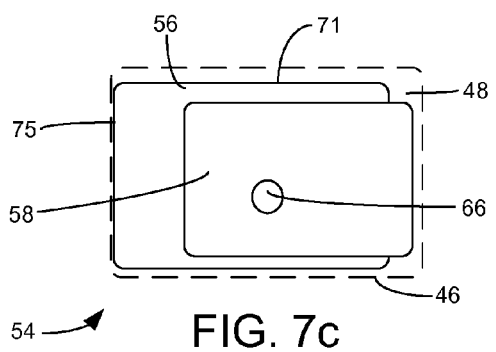

FIG. 7c is a plan view of another embodiment of active electrode 54. Active electrode 54 may be made up of the same elements as were employed in active electrode 54 in FIG. 7a. In contrast thereto, however, while backing layer 56 continues to be covered in part only by pH-control layer 58, periphery 75 of pH-control layer 58 extends to the exterior of periphery 71 of backing layer 56. These are nonetheless acceptable relationships among components in an active electrode.

Figure 7D:
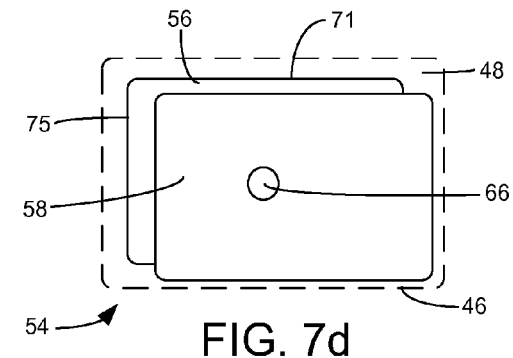

FIG. 7d is a plan view of another embodiment of active electrode 54. Active electrode 54 may be made up of the same elements as were employed in active electrode 54 in FIG. 7a. In FIG. 7d by contrast, a pH-control layer 58 may be included in active electrode 130 that may be of approximately the same size and shape as backing layer 56. Thus, pH-control layer 58 may have a periphery 75 approximately congruent with periphery 71 of backing layer 56. These nonetheless are acceptable relationships among components in an active electrode. Indeed, in some embodiments, pH-control layer 58 may entirely cover backing layer 56 or even exceed it in size. The total area of backing layer 56 may be approximately equal to the area of pH-control layer 58. Backing layer 56 may have an exposed area that is not covered by pH-control layer 58 between periphery 75 of pH-control layer 58 and periphery 71 of backing layer 56, or backing layer 56 may be entirely covered by pH-control layer 58.

Figure 7E:
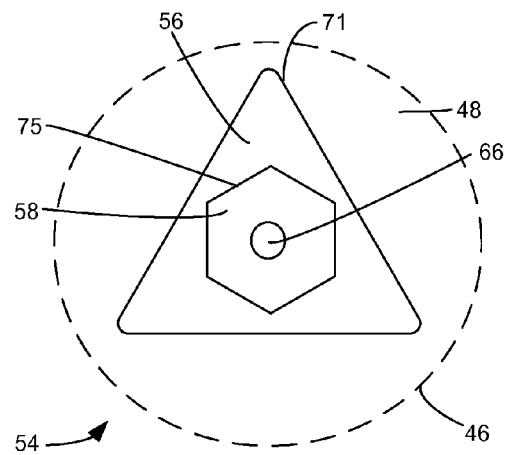

FIG. 7e is a plan view of another embodiment of an active electrode 54. Active electrode 54 may be made up of the same elements as were employed in active electrode 54 in FIG. 7a, in addition to a backing layer 56 may have a generally triangular shape with a periphery 71 having three vertices, and pH-control layer 58 having a generally hexagonal shape along periphery 75. The periphery 48 of solution matrix 46 is shown has forming a generally circular shape.

Figure 7F:
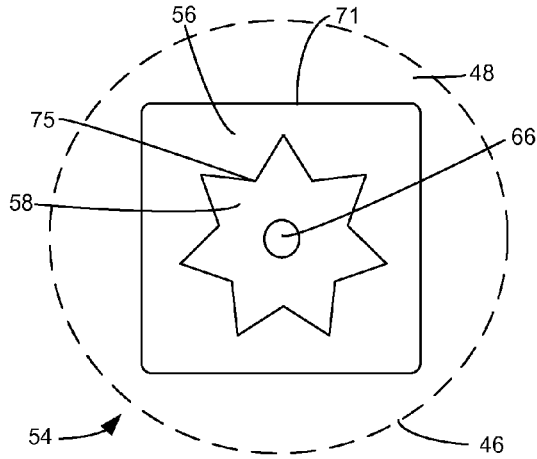

FIG. 7f is a plan view of another embodiment of an active electrode 54. Active electrode 54 of the same elements as were employed in active electrode 54 in FIG. 7a, in addition to a backing layer 56 having a generally squarish shape about periphery 71 with rounded corners and a pH-control layer 58 having a star-shaped, polygonal shape about periphery 75 with seven points. The periphery 48 of solution matrix 46 is shown has forming a generally circular shape.

Of course, in other embodiments, backing layer 56, pH-control layer 58, and solution matrix 46 may have any desirable shape relative to each other. Additionally, pH-control layer 58 may be provided with any number of a variety of patterns. Such patterns may allow for targeted and shaped current flow $I_S$ to a desired portion of the brain for treatment. In some embodiments, a crescent shape, or other shape may also be provided. Similarly, if a particular portion of the brain targeted for treatment has a particular shape, the pH-control layer and overall size of the electrode may be formed to effectively treat the targeted portion.

FIGS. 8a-8d are plan views of individual embodiments of various designs of pH control layers of active electrodes in an active electrode patch. In each case, the active electrode may be shown resting against, and possibly secured to, the underlying therapeutic face of a substrate, such as those discussed above. In the assembled condition of the electrode patch in which the active electrode may be employed, a medicament matrix would be superimposed over the active electrode and pH control layer and secured about the periphery of the active electrode to therapeutic face 180 entirely obscuring the active electrode.

Figure 8A:
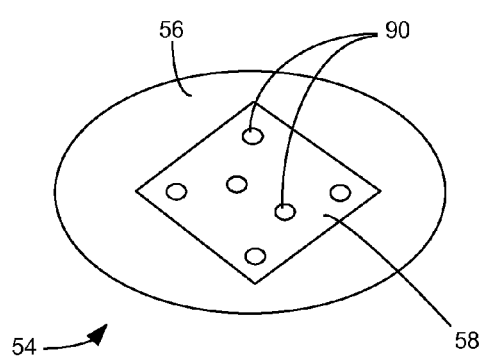
FIGS. 8a-8d illustrate various embodiments of layer design for pH-control layers and backing layers of exemplary electrode patches.

FIG. 8a is such a plan view of another embodiment of an active electrode 54. Active electrode 54 may include a backing layer 56 having a generally oval periphery 71. Superimposed on backing layer 56 may be a pH-control layer 58 that has a generally rhomboidal periphery 75. Formed through pH-control layer 58 may be a plurality of apertures 90 at which the surface of backing layer 56 against which pH-control layer 258 may be disposed may be nonetheless free of pH-control layer 258.

Figure 8B:
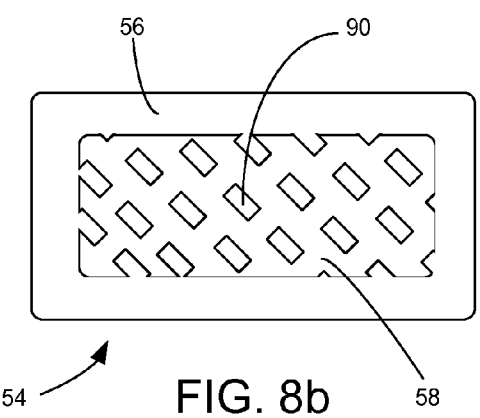

FIG. 8b is a plan view of another embodiment of an active electrode 54 incorporating teachings of the present invention. Active electrode 54 may include backing layer 56 having a generally rectangular periphery 71 with beveled corners. A pH-control layer 58 of overall, generally rectangular extent may be formed in a lattice with apertures 90.

Figure 8C:
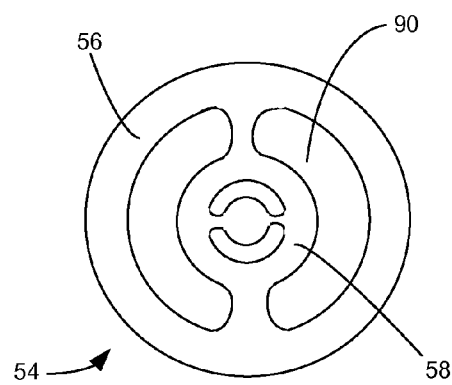

Similarly, FIG. 8c is a plan view of another embodiment of active electrode 84 include a backing layer 56 having a generally circular periphery 71, and a pH-control layer 58 of an overall, generally circular extent with a periphery 75 that may be congruent to and coincident with periphery 71 of backing layer 56. In detail, however, pH-control layer 276 may be made up of a plurality of discrete components that cover a plurality of complex shapes.

Figure 8D:
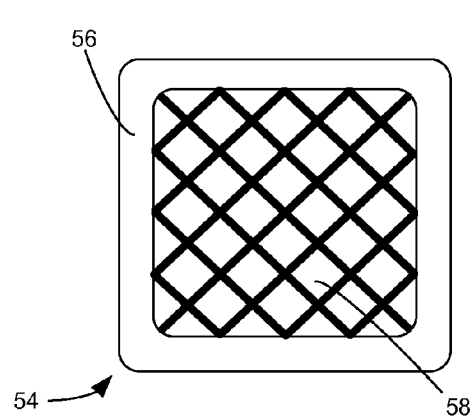

FIG. 8d is a plan view of another embodiment of an active electrode 54 including a backing layer 56 having a generally square-shaped periphery 71 with rounded corners. Superimposed on backing layer 56 may be pH-control layer 58 formed in a series of smaller, unconnected squares.

In some embodiments, therapeutic agents and medicaments may be employed in an iontophoretic medicament delivery process along with the TDCS process. U.S. Pat. No. 8,197,844 discusses iontophoretic transfer of medicament and is incorporated herein by reference in its entirety. In some embodiments, the addition of medicament delivery may enhanced the effectiveness or efficiency of the TDCS process. In other embodiments, more than one cathode or anode or both may be applied to the head of a patient to alter or expand the current flow through the head of the patient to treat particular areas during a TDCS treatment.

Finally, methods of manufacture necessary to provide the inventive embodiments described above, as well as methods associated with the effective therapeutic use of any of those inventive embodiments are anticipated by this disclosure.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

What is claimed:

1. A noninvasive transcranial direct current brain stimulation apparatus for use in providing electrical stimulation to the surface of a patient's head in order to deliver electrical currents to the patient's brain to modify brain function, the apparatus comprising:

a current generator configured to generate electrical current suitable for performing transcranial direct current brain stimulation through a patient's head to the patient's brain by passing said current through a specially-configured electrode patch, an anode patch in electrical communication with said current generator and being noninvasively attachable to a first location on patient's head and which can establish electrical connection therewith, a cathode patch in electrical communication with said current generator and being noninvasively attachable to a second location on a patient's head which can establish electrical connection therewith, said first location and second location being capable of being spaced apart from each other so that a short circuit between said anode and said cathode is not created, said anode patch, said cathode patch, and said electrical generator being configured to form an electrical circuit among them using the patient's brain as a conductive medium in order to cause electrical current to flow between said anode patch and said cathode patch through said patient's brain to modify brain function, said anode patch and said cathode patch each including
- a flexible, planar, non-conductive, biocompatible substrate having a driving face,
- a backing layer adjacent said driving face of said flexible, planar biocompatible substrate,
- a planar solution matrix located on said driving face of said flexible, planar biocompatible substrate,
- a pH control layer formed in said solution matrix, said pH control layer comprising Ag and AgCl, said Ag and AgCl serving to control pH levels of said solution matrix when electrical power is transmitted between said anode patch and said cathode patch through a patient's brain,
- a skin contact surface on a first side of said planar solution matrix, said skin contact surface being configured for attachment to skin of said patient's head, said skin contact surface being electrically conductive with respect to skin of said patient's head,
- said skin contact surface serving as a means to effect an electrically conductive engagement with skin of a patient,
- a securement surface on a second side of said planar solution matrix, said solution matrix being retained in proximity with said planar biocompatible substrate by said securement surface,
- an access aperture located on said patch extending through said substrate and through said backing layer, and
- an electrical contact projecting through said access aperture, said access aperture being of the type to which electrical leads can be readily secured and non-destructively disengaged in order to establish electrical communication between said solution matrix and skin of a patient's head in order to cause electrical currents to travel through said electrical contact, through said solution matrix, through skin of a patient's head and into a patient's brain, wherein said transcranial direct current brain stimulation apparatus is configured to provide electrical stimulation to the surface of a patient's head in order to deliver electrical currents to the patient's brain that are therapeutically sufficient in order to achieve a desired therapeutic effect on the patient, wherein said electrical circuit can cause between 0.5 mA and 3 mA of electrical current to flow through said patient's brain for a non-trivial period of time to achieve said desired therapeutic effect wherein said therapeutic effect is selected from the group consisting of: causing excitability diminution, causing excitability enhancement, altering neural activity, altering patient behavior, ameliorating a psychiatric condition, ameliorating depression, reducing manic symptom, and modulating human cerebral cortical function.

2. The apparatus of claim 1, further comprising a saline solution in said solution matrix.

3. The apparatus of claim 1, wherein said backing layer includes a material selected from the group consisting of carbon and copper.

4. The apparatus of claim 1, wherein said pH-control layer has a repeating pattern of apertures on it.

5. The apparatus of claim 1 further comprising a hollow stud on said pH control layer, and a shaft press fit into said hollow stud, said shaft being in electrical communication with said electrical contact.

* * * * *